(12) United States Patent
Judson et al.

(10) Patent No.: US 7,762,990 B2
(45) Date of Patent: Jul. 27, 2010

(54) SURGICAL ACCESS APPARATUS WITH CENTERING MECHANISM

(75) Inventors: Jared Alden Judson, Topsfield, MA (US); Oivind Brockmeier, Middlesex, MA (US); Kenneth Allen Focht, Needham, MA (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/124,624

(22) Filed: May 21, 2008

(65) Prior Publication Data

US 2008/0294112 A1 Nov. 27, 2008

Related U.S. Application Data

(60) Provisional application No. 60/931,768, filed on May 24, 2007.

(51) Int. Cl.
*A61M 5/178* (2006.01)
(52) U.S. Cl. .................................. 604/167.06
(58) Field of Classification Search ............ 604/167.06, 604/256, 264, 165.05, 167.01, 164
See application file for complete search history.

(56) References Cited

U.S. PATENT DOCUMENTS

| | | | |
|---|---|---|---|
| 4,795,426 A | 1/1989 | Jones | |
| 4,943,280 A | 7/1990 | Lander | |
| 5,127,909 A | 7/1992 | Shichman | |
| 5,180,373 A | 1/1993 | Green et al. | |
| 5,209,737 A | 5/1993 | Ritchart et al. | |
| 5,342,315 A | 8/1994 | Rowe et al. | |
| 5,360,417 A | 11/1994 | Gravener et al. | |
| 5,389,081 A * | 2/1995 | Castro ................ | 604/167.03 |
| 5,397,314 A | 3/1995 | Farley et al. | |
| 5,407,433 A | 4/1995 | Loomas | |
| 5,484,418 A | 1/1996 | Quiachon et al. | |

(Continued)

FOREIGN PATENT DOCUMENTS

EP 1702575 9/2006

(Continued)

OTHER PUBLICATIONS

European Search Report dated Aug. 29, 2008, Application No. EP 08 25 1778.

(Continued)

*Primary Examiner*—Nicholas D Lucchesi
*Assistant Examiner*—Brooke M Matney

(57) ABSTRACT

A surgical access apparatus includes a housing member and a portal member extending from the housing member and defining a longitudinal axis. The housing member and the portal member define a longitudinal passage therethrough dimensioned to permit passage of an elongated object. A centering mechanism is mounted relative to the housing member. The centering mechanism includes an annular element mounted for rotational movement within the housing member and about the longitudinal axis and first and second arm elements mounted to the annular element and extending radially inwardly relative to the longitudinal axis. The first and second arm elements are each positioned to intersect the longitudinal passage and are adapted to pivot relative to the housing member. The first and second arm elements are operatively connected whereby pivotal movement of the first arm element upon engagement with the elongated object causes the annular element to rotate in response thereto and effect corresponding pivotal movement of the second arm element.

15 Claims, 5 Drawing Sheets

U.S. PATENT DOCUMENTS

| | | | |
|---|---|---|---|
| 5,492,304 | A | 2/1996 | Smith et al. |
| 5,549,565 | A | 8/1996 | Ryan et al. |
| 5,603,702 | A | 2/1997 | Smith et al. |
| 5,634,908 | A | 6/1997 | Loomas |
| 5,657,963 | A | 8/1997 | Hinchliffe et al. |
| 5,685,854 | A | 11/1997 | Green et al. |
| 5,720,759 | A | 2/1998 | Green et al. |
| 5,722,958 | A | 3/1998 | Gravener et al. |
| 5,727,770 | A | 3/1998 | Dennis |
| 5,752,970 | A | 5/1998 | Yoon |
| 5,820,600 | A | 10/1998 | Carlson et al. |
| 5,895,377 | A | 4/1999 | Smith et al. |
| 6,228,061 | B1 | 5/2001 | Flatland et al. |
| 6,383,160 | B1 | 5/2002 | Madsen |
| 6,458,103 | B1 | 10/2002 | Albert et al. |
| 7,025,747 | B2 | 4/2006 | Smith |
| 7,063,685 | B2 | 6/2006 | Rome |
| 2002/0072713 | A1 | 6/2002 | Almond et al. |
| 2003/0187397 | A1 | 10/2003 | Vitali |
| 2004/0064100 | A1 | 4/2004 | Smith et al. |
| 2004/0082969 | A1 | 4/2004 | Kerr |
| 2005/0165281 | A1 | 7/2005 | Ravikumar |
| 2006/0020281 | A1 | 1/2006 | Smith |
| 2006/0047284 | A1 | 3/2006 | Gresham |
| 2008/0091144 | A1 | 4/2008 | Moran et al. |

FOREIGN PATENT DOCUMENTS

| | | |
|---|---|---|
| WO | 01/52754 | 7/2001 |

OTHER PUBLICATIONS

European Search Report dated Sep. 4, 2008, Application No. EP 08 25 1791.

European Search Report for corresponding EP 08251778 date of mailing is Sep. 8, 2008 (3 pages).

European Search Report, Application No. EP 09251622, dated Oct. 23, 2009.

* cited by examiner

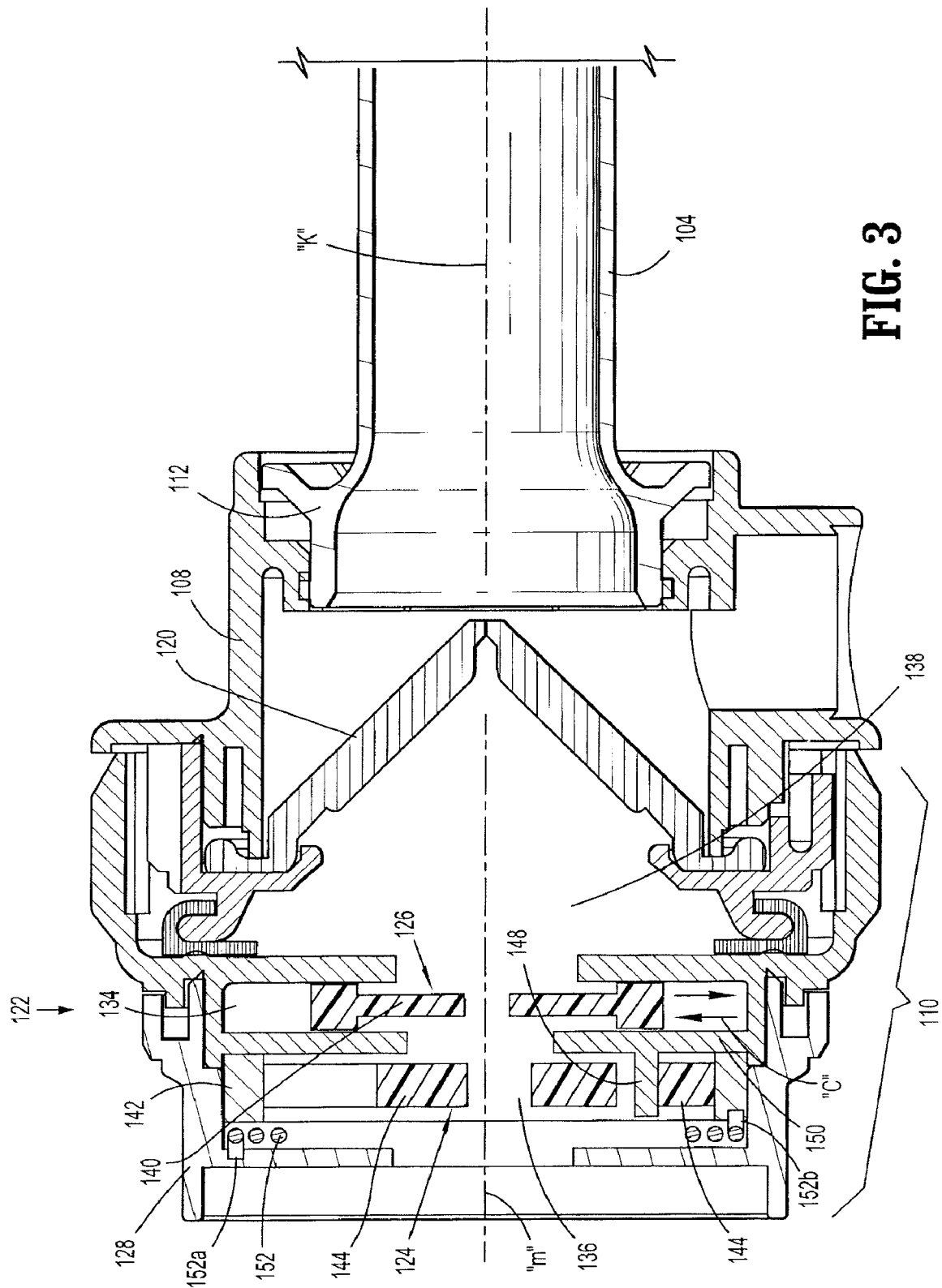

SURGICAL ACCESS APPARATUS WITH CENTERING MECHANISM

CROSS REFERENCE TO RELATED APPLICATION

The present application claims the benefit of and priority to U.S. Provisional Application Ser. No. 60/931,768 filed on May 24, 2007, the entire contents of which are incorporated herein by reference.

BACKGROUND

1. Technical Field

The present disclosure relates to a surgical portal for accessing underlying body tissue to permit the introduction of surgical objects in conjunction with a medical procedure. More particularly, the present disclosure relates to a surgical portal including a centering mechanism for facilitating the alignment of a surgical instrument with an axis of the surgical portal, to thereby assist in the maintenance of the seal about the instrument and/or the minimize lateral movement of the instrument within the portal.

2. Discussion of Related Art

Surgical portals are employed in various minimally invasive procedures including laparoscopic or endoscopic procedures. Such portals are inclusive of trocar cannulas, catheters, or, in the event of a minimally invasive hand assist procedures, hand access devices. Surgical portals typically incorporate a seal mechanism to form a fluid tight seal about an instrument or hand passed through the portal. The seal mechanisms, however, often are limited by their ability to sustain a seal when an instrument, particularly, a smaller diameter instrument, is moved off-axis relative to a central axis of the portal. Moreover, the seal mechanisms are also limited by their ability to sustain their integrity when the surgical instrument is angulated. Such extreme ranges of motion of smaller diameter surgical instruments within the portal can create a "cat eye" or crescent shaped gap about the instrument resulting in fluid loss (e.g., insufflation gas loss).

SUMMARY

Accordingly, the present disclosure is directed to a surgical access apparatus including a housing member and a portal member extending from the housing member and defining a longitudinal axis. The housing member and the portal member define a longitudinal passage therethrough dimensioned to permit passage of an elongated object. A centering mechanism is mounted relative to the housing member. The centering mechanism includes an annular element mounted for rotational movement within the housing member and about the longitudinal axis and first and second arm elements mounted to the annular element and extending radially inwardly relative to the longitudinal axis. The first and second arm elements are each positioned to intersect the longitudinal passage and are adapted to pivot relative to the housing member. The first and second arm elements are operatively connected whereby pivotal movement of the first arm element upon engagement with the elongated object causes the annular element to rotate in response thereto and effect corresponding pivotal movement of the second arm element. A seal may be disposed within the housing member. The seal is adapted to establish a substantial sealing relation with the elongated object. The first and second arm elements may be normally biased to urge the instrument toward a generally aligned position with respect to the longitudinal axis.

The centering mechanism may include a third arm element. The first, second and third arm elements may be generally coaxially arranged with respect to the longitudinal axis.

The annular element may include an outer element with the first and second arm elements being connected to the outer element. The first and second arm elements are adapted to pivot about respective pivotal axes upon rotation of the outer element.

In an alternate embodiment, the annular element may include an inner element. The first and second arm elements are adapted to pivot upon rotation of the inner element. An outer mount may be provided where the first and second arm elements being pivotally mounted to the outer mount. The outer mount is fixed with respect to the housing member. The first and second arm elements may be each pivotally mounted to the outer mount through a living hinge.

In another embodiment, the surgical access apparatus includes a housing member, a portal member extending from the housing member and defining a longitudinal axis with the housing member and the portal member defining a longitudinal passage therethrough dimensioned to permit passage of an elongated object and at least three arm elements pivotally mounted relative to the housing member and extending radially inwardly relative to the longitudinal axis. The at least three arm elements are each positioned to intersect the longitudinal passage. The at least three arms have camming structure to operatively connect the at least three arms in a manner whereby pivotal movement of a first arm element upon engagement with the elongated object causes corresponding pivotal movement of the remaining arm elements. A seal may be disposed within the housing member. The seal is adapted to establish a substantial sealing relation with the elongated object. The at least three arm elements may be pivotally mounted relative to the housing member about living hinges. Each of the at least three arm elements may include cam slots for receiving corresponding cam pins of adjacent arm elements. The at least three arm elements may be adapted to normally bias the elongated object in a generally aligned position with respect to the longitudinal axis.

BRIEF DESCRIPTION OF THE DRAWINGS

Preferred embodiments of the present disclosure will be better appreciated by reference to the drawings wherein:

FIG. 3 is a side cross-sectional view of the housing member and the centering mechanism;

DETAILED DESCRIPTION OF THE EMBODIMENTS

The access apparatus of the present disclosure is capable of accommodating objects of varying diameters, e.g., including instruments from about 4.5 millimeter (mm) to about 15 millimeter (mm), during a minimally invasive surgical procedure. Moreover, the access apparatus contemplates the introduction and manipulation of various types of instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the access apparatus includes a centering mechanism which while permitting angular manipulation of the surgical instrument normally biases the instrument into an aligned position with respect to the axis of the cannula. This feature of the present disclosure desirably minimizes the entry and exit of gases and/or fluids to/from the body cavity.

Examples of instrumentation contemplated for use with the access apparatus include clip appliers, graspers, dissectors, retractors, staplers, laser probes, photographic devices, endoscopes and laparoscopes, tubes, and the like. Such instruments will be collectively referred to herein as "instruments or instrumentation".

In the following discussion, the term "proximal" will refer to the portion of the access apparatus nearest to the clinician during operation while the term "distal" will refer to that portion of the access apparatus most remote to the clinician.

Figure 1:
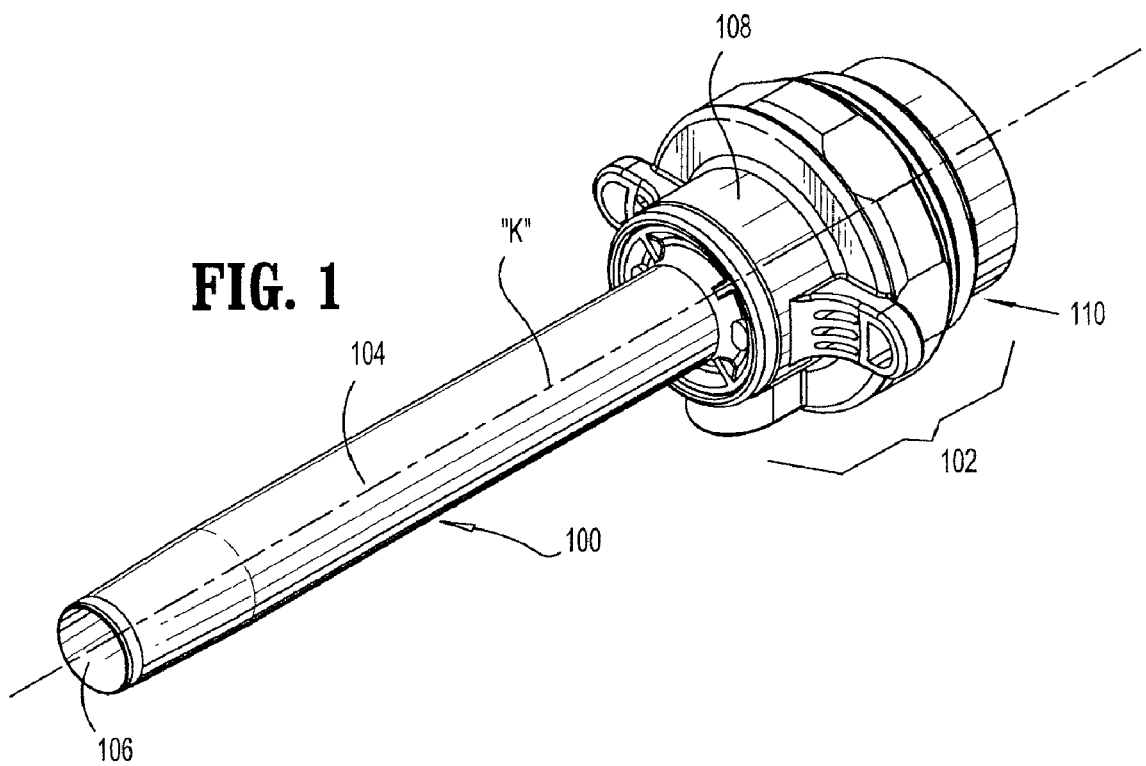
FIG. 1 is a perspective view of the surgical access apparatus in accordance with the principles of the present disclosure.
Figure 2:
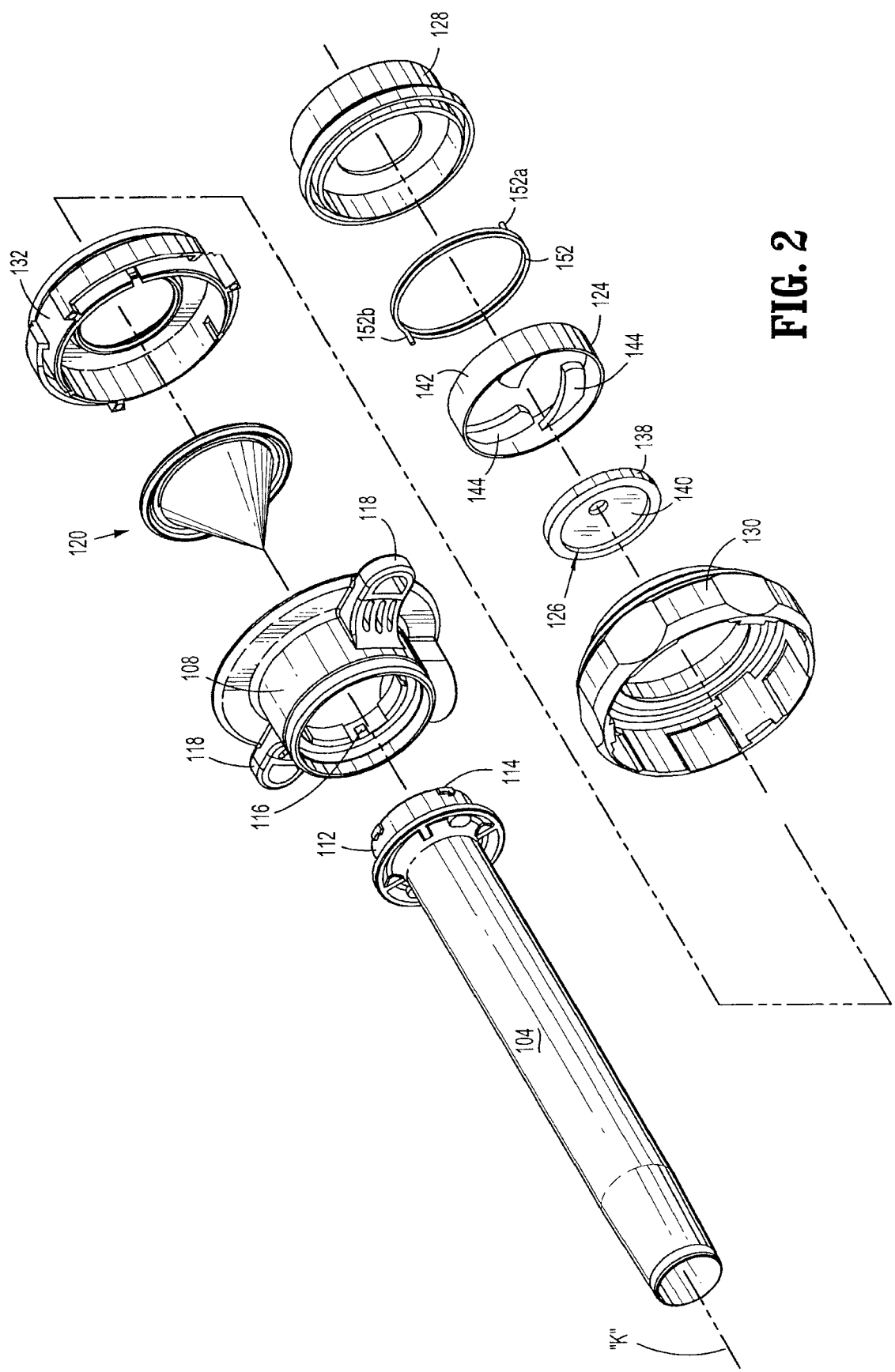
FIG. 2 is a perspective view with parts separated of the surgical access apparatus of FIG. 1 illustrating the housing member, portal member and the centering mechanism.

Referring now to the drawings, in which like reference numerals identify identical or substantially similar parts throughout the several views, FIGS. 1-2 illustrate the access apparatus 100 of the present disclosure. Access apparatus 100 may be any member suitable for the intended purpose of accessing a body cavity and typically defines a passageway permitting introduction of instruments or the clinician's hand therethrough. Access apparatus 100 is particularly adapted for use in laparoscopic surgery where the peritoneal cavity is insufflated with a suitable gas, e.g., $CO_2$, to raise the cavity wall from the internal organs therein. Access apparatus 100 is typically used with an obturator assembly (not shown) which may be blunt, a non-bladed, or a sharp pointed instrument positionable within the passageway of the access apparatus 100. The obturator assembly is utilized to penetrate the abdominal wall to introduce the access apparatus 100 through the abdominal wall, and then subsequently is removed from the access apparatus 100 to permit introduction of the surgical instrumentation utilized to perform the procedure through the passageway.

Access apparatus 100 includes housing member 102 and portal member 104 connected to the housing member 102 and extending therefrom. Portal member 104 defines a longitudinal axis "k" extending along the length of the portal member 104. Housing member 102 and portal member 104 further define internal longitudinal passage 106 dimensioned to permit passage of surgical instrumentation. Portal member 104 may be formed of any suitable medical grade material, such as stainless steel or other rigid materials, including polymeric materials, such as polycarbonate, or the like. Portal member 104 may be transparent or opaque. The diameter of portal member 104 may vary, but typically ranges from about 4.5 millimeters (mm) to about 15 millimeters (mm).

Housing member 102 may include a number of components assembled together to define the outer housing shown in the drawings. For example, housing member 102 may include main housing 108 and centering assembly 110. Centering assembly 110 may or may not be a component of housing member 102. In one embodiment, centering assembly 110 may be selectively releasably mountable to main housing 108. In another embodiment, centering assembly 110 is an integral part of main housing 108. Centering assembly 110 will be discussed in greater detail hereinbelow. Main housing 108 is attached to the proximal end of portal member 104, specifically, to portal flange 112 of portal member 104. In one method, main housing 108 is connectable to portal flange 112 through a bayonet coupling consisting of radially spaced tongues 114 on the exterior of portal flange 112 and corresponding recesses 116 within the interior of main housing 108, which are arranged to receive the tongues 114. Thereafter, portal flange 112 and main housing 108 are rotated to securely lock tongues 114 within recesses 116. Other conventional means, e.g., a threaded connection, snap fit, ultrasonic welding or any other means envisioned by one skilled in the art including, e.g., adhesive means, may be utilized to connect portal flange 112 and main housing 108. Main housing 108 further includes diametrically opposed housing grips 118 dimensioned and arranged for gripping engagement by the fingers of the user. Additionally or alternatively, suture anchors may extend from main housing. Portal flange 112 and main housing 108 may be integrally formed with portal member 104.

Main housing 108 further includes valve 120. Valve 120 may be a zero-closure valve such as duck-bill valve having a slit which is adapted to close in the absence of a surgical object and/or in response to insufflation gases of the pressurized cavity. In the alternative, valve 120 may be a gel seal, balloon valve, or a flapper valve.

Referring now to FIGS. 1-3, centering assembly 110 includes centering housing, generally identified as reference numeral 122, centering mechanism 124 and seal 126 which are each disposed within the centering housing 122. Centering housing 122 defines central housing axis "m" which is preferably parallel to the axis "k" of portal member 104, and, more specifically, coincident with the axis "k" of the portal member 104. Centering housing 122 incorporates three housing components, namely, first, second and third housing components 128, 130, 132, respectively, which, when assembled together, form the centering housing 122. Assembly of housing components 128, 130, 132 may be affected by any of the aforementioned connection means discussed with respect to main housing 108. Although shown and described as three components, it is appreciated that centering housing 122 may be a single component having centering mechanism 124 and seal 126 mounted therein. In the assembled condition of housing components 128, 130, 132, internal seal chamber 134 and internal centering chamber 136 are defined within the walls of centering housing 122.

Centering assembly 110 includes seal 126 disposed within internal seal chamber 134. Seal 126 may include annular support collar 138 and seal element 140 which is mounted within, or attached to, the support collar 138. Support collar 138 is adapted to reciprocally slide in the direction of directional arrows "c" (FIG. 3) within internal seal chamber 134 in general transverse relation to central housing axis "m". Support collar 138 may comprise a plastic, metallic or elastomer material and may be monolithically formed with seal element 140. Support collar 138 may comprise a two-part ring assembly such as the assembly disclosed in certain embodiments of commonly assigned U.S. Pat. No. 6,702,787 to Racenet, the entire disclosure of which is hereby incorporated by reference herein. The ring members have holes and posts that are arranged for mating with one another, joining the ring members together with the seal element fixed therebetween. Seal element 140 is preferably a septum seal including an inner area defining a central aperture for sealed reception of a surgical instrument. The periphery of seal element 140 is preferably secured to, or within, support collar 138. Consequently, seal element 140 may move with support collar 138 within internal seal chamber 134 during manipulation of the inserted object. Any means for securing seal element 140 to support collar 138 are envisioned including with the use of cements, adhesives, etc. Seal element 140 may comprise an elastomeric material and may, or may not, include a fabric layer juxtaposed with the elastomeric material. For example, in one embodiment, seal element 140 desirably comprises an elastomeric material compression-molded with a fabric material such as disclosed in certain embodiments of the aforementioned U.S. Pat. No. 6,702,787. The fabric may comprise a woven, knitted, braided, or non-woven material of polymeric materials. Alternatively, seal element 140 may comprise a gel material fabricated from soft urethane gel, silicon gel, etc. As noted above, seal element 140 and support collar 138 may be monolithically formed as a single unit. In a further embodiment, seal element 140 and support collar 138 may be formed of one or more elastomers.

Figure 5:
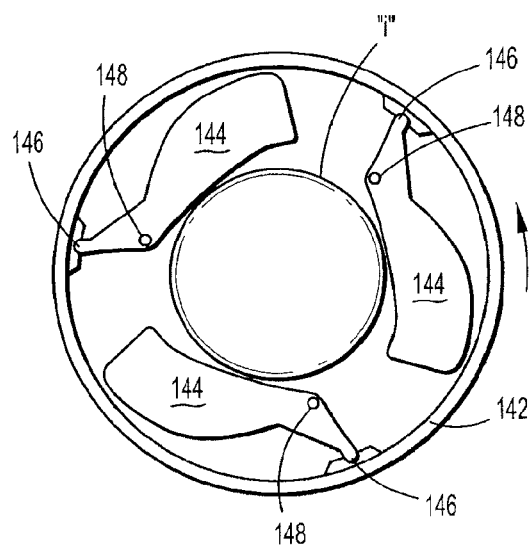
FIG. 5 is a top plan view similar to the view of FIG. 4 illustrating a large diameter instrument positioned within the centering mechanism.
Figure 4:
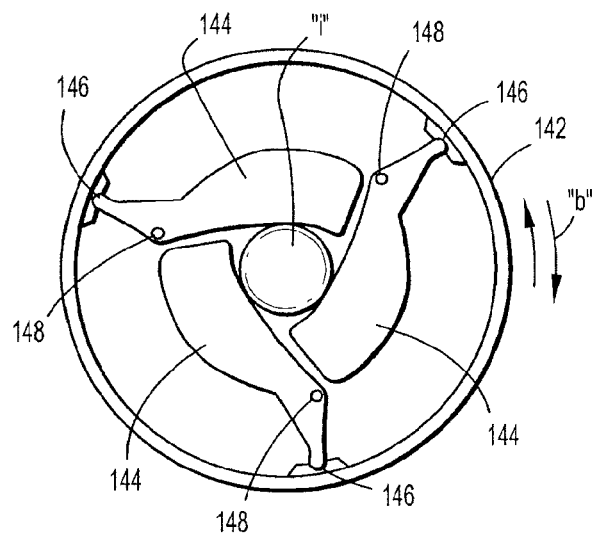
FIG. 4 is a top plan view of the centering mechanism illustrating the annular element and the centering arms extending inwardly from the annular element and having a small diameter instrument positioned therein.

Referring now to FIGS. 4-5, in conjunction with FIGS. 2-3, centering mechanism 124 will be discussed in detail. Centering mechanism 124 is disposed within internal centering chamber 136 of centering housing 122. In one embodiment, centering mechanism 124 is proximal of seal 126; however, it is envisioned that the centering mechanism 124 also may be distal of the seal 126. Centering mechanism 124 includes ring or annular element 142 and a plurality of arm elements 144 connected to the annular element 142 and extending radially inwardly relative to axis "m". Annular element 142 may be formed of any rigid material including a suitable polymeric material or metal. Annular element 142 is adapted for limited rotational movement in the direction of directional arrows "b" within internal centering chamber 136 about axis "m". Arm elements 144 are operatively connected to annular element 142 through a hinge 146 or the like whereby each arm element 144 may pivot or rotate about the hinge 146 during operation. In one embodiment, hinge 146 may include a ball and socket arrangement. Each arm element 144 is also mounted relative to centering housing 122 through respective pivot pins 148 to pivot about the pins 148 during rotation of annular element 142. Pivot pins 148 extend through corresponding openings in the respective arm elements 144 and are secured to centering housing 122, specifically, plate 150 of centering housing 122 in fixed relation therewith (FIG. 3). Centering mechanism 124 further may include torsion spring 152 adjacent annular element 142. Torsion spring 152 is fixed at one end 152a to housing component 128 and at its other end 152b to annular element 142. In this manner, torsion spring 152 normally biases annular element 142 in a clockwise direction relative to FIG. 4.

The use access apparatus 100 in connection with introduction of a surgical instrument "i" will be discussed. Centering assembly 110 is mounted to housing member 102 if not an integral component of the housing member 102. Access apparatus 100 is introduced into an insufflated abdominal cavity typically utilizing a sharp or non-bladed obturator (not shown) positioned within longitudinal passage 106 of access apparatus 100. The obturator is then removed leaving access apparatus 100 to thereby define a portal to the underlying tissue within the abdominal cavity. With reference to FIG. 4, an object, e.g., a surgical instrument "i" is inserted into centering assembly 110, through centering mechanism 124 and seal 126 whereby the portions defining the aperture of seal element 140 stretches to accommodate the instrument "i" in substantial sealed relation therewith. Simultaneous with the insertion of the instrument "i", at least one of arm elements 144 of centering mechanism 124 initially pivot about its/their respective pivot pins 148 in a radially outward direction relative to housing axis "m". This movement of arm element 144 thereby causes annular element 142 (directional arrows "b") to rotate about housing axis "m" in a counterclockwise direction relative to FIG. 4 against the bias of torsion spring 152 to permit the centering mechanism 124 to receive the surgical instrument "i". Specifically, rotational movement of annular element 142 causes each of arm elements 144 to simultaneously pivot about their respective pivot pins 148 in a radial outward direction relative to housing axis "m". Additionally, torsion spring 152 enters a stressed state, and, therefore, applies a biasing force to continually bias annular element 142 in the opposite rotational direction, i.e., in a clockwise direction relative to FIG. 4. This angular biasing force on annular element 142 also causes arm elements 144 to be biased to pivot about their respective pivot pins 148 in a radial inward or clockwise direction relative to housing axis "m". In this manner, the instrument "i" is captured between arm elements 144 with the arm elements 144 positioning the instrument "i" into generally aligned relation with respect to the housing axis "m". The aligned relation of the instrument "i" substantially minimizes the potential of "cat eyeing" of seal 126 and undesired release of gases through the seal 126.

FIG. 5 illustrates insertion of a relatively large diameter instrument "i" through centering mechanism 122. During insertion, annular element 142 rotates through a greater angular sector of rotation and arm elements 144 correspondingly pivot through a greater range of pivotal motion to permit reception of the large instrument "i". Torsion spring 152 continually biases annular element 142 to its initial position which causes arm elements 144 to cooperatively engage and bias the instrument "i" into aligned position with housing axis "m".

Figure 7:
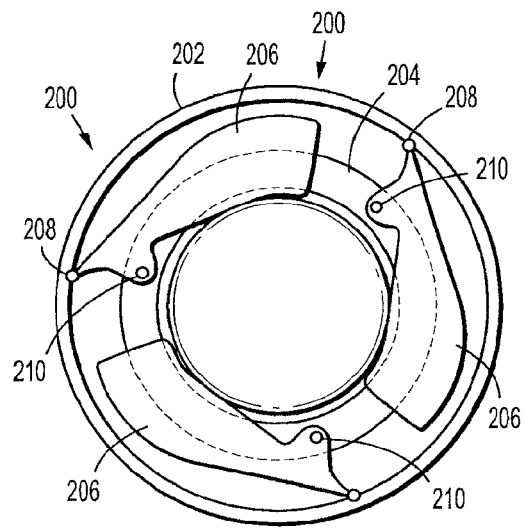
FIG. 7 is a top plan view similar to the view of FIG. 6 illustrating the centering mechanism with a large diameter instrument positioned therein.
Figure 6:
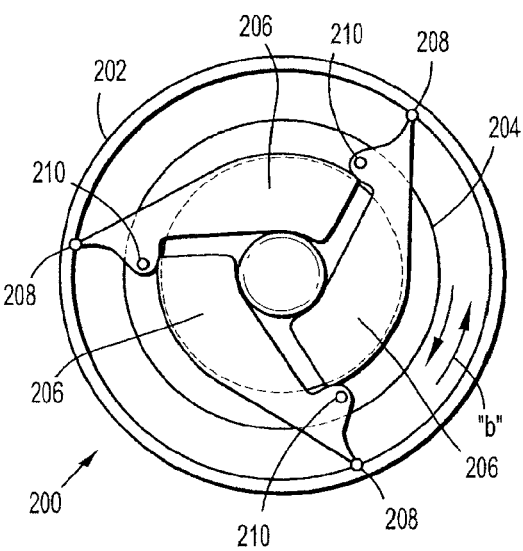
FIG. 6 is a top plan view of an alternate embodiment of the centering mechanism illustrating an outer element, an inner element and centering arms connected to the inner element.

FIGS. 6-7 illustrate an alternate embodiment of centering mechanism. Centering mechanism 200 includes outer annular element 202, inner annular element 204 and arm elements 206. Outer annular element 202 is fixed within centering housing 122, and, thus does not rotate within the housing 122. Inner annular element 204 is adapted for limited rotational movement within centering housing 122 relative to housing axis "m". Arm elements 206 are connected to outer annular element 202 through hinges 208 and may pivot about the hinges 208 relative to the outer annular element 202. Any means for pivotally mounting arm elements 206 to outer annular element 202 are envisioned. In one embodiment, arm elements 206 are mounted to outer annular element 202 through a living hinge. Arm elements 206 are adapted to pivot relative to outer annular element 202 and centering housing 122 about pivot pins 210. Pivot pins 210 extend through arm elements 206 and are connected to inner annular element 204. During operation, an instrument "i" is advanced through arm elements 206. At least one of arm elements 206 engages the instrument "i" and pivots radially outwardly relative to housing axis "m". This pivoting motion causes inner annular element 204 to correspondingly rotate in a clockwise direction of directional arrows "b" (FIG. 6) through its interconnection with pivot pins 210, which causes simultaneous pivotal movement of all of the arm elements 206 to permit passage of the instrument "i". In this embodiment, torsion spring 152 is connected to inner annular element 204 and to centering housing 122 to normally bias the inner annular element 204 in a clockwise direction upon rotational movement of inner annular element 204. This biasing causes arm elements 206 to impart a radially inward force to the instrument "i" to position the instrument "i" into generally aligned position with respect to the longitudinal axis "m". FIG. 7 illustrates the insertion of a large diameter instrument and the corresponding counterclockwise rotational movement of inner annular element 204 through a greater sector of rotation and corresponding pivotal movement of arm elements 206.

Figure 8:
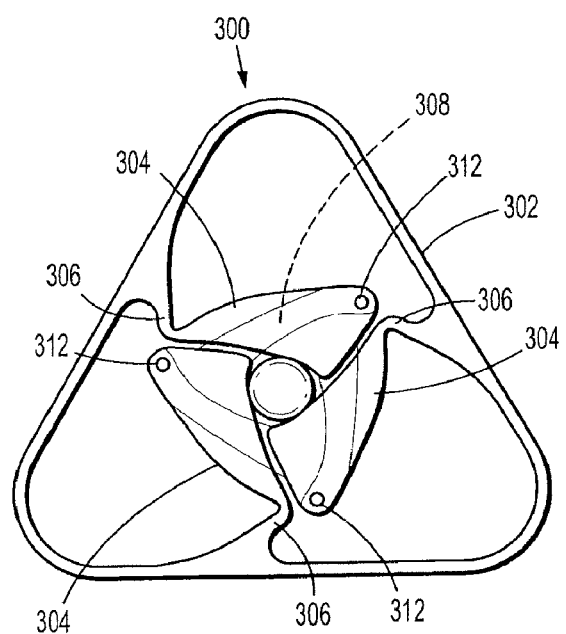
FIG. 8 is a top plan view of an alternate embodiment of the centering mechanism illustrating an outer element, centering arms connected to the inner element and having a camming mechanism for causing movement of the centering arms.
Figure 9:
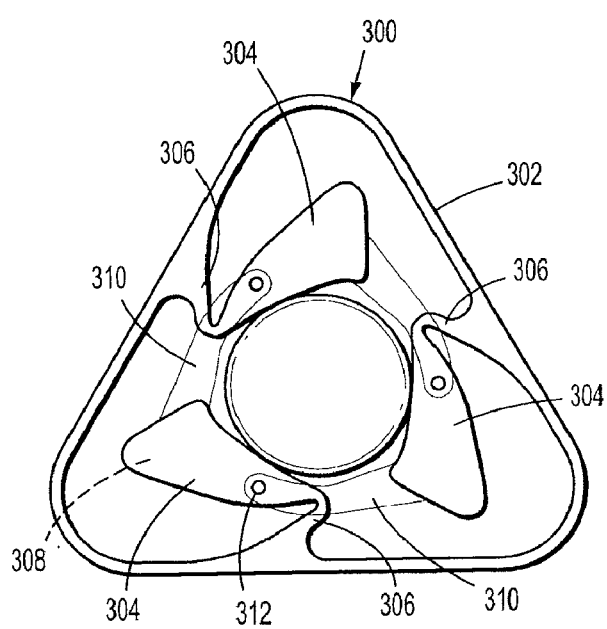
FIG. 9 is a top plan view similar to the view of FIG. 8 illustrating the centering mechanism with a large diameter instrument positioned therein.

FIGS. 8-9 illustrate an alternate embodiment of the centering mechanism of the present disclosure. Centering assembly 300 includes outer element 302 which is fixed within centering housing 122 and a plurality, e.g., three, of arm elements 304 extending radially inwardly from the outer element 302. Arm elements 304 are connected to outer element 302 via living hinges 306 and may pivot about the living hinges 306 during insertion of the instrument "i". Each arm element 304 includes cam slot or recess 308 formed on its lower or distal surface. Arm elements 304 further include cam arms 310 connected thereto, and, possibly integrally formed therewith. Cam arms 310 include cam pins 312 connected thereto and received within corresponding cam slots 308 of adjacent arm elements 304. During insertion of the instrument "i", cam pins 312 of each cam arm 310 traverses cam slots 308 of an adjacent arm element 306 to simultaneously radially displace relative to housing axis "m" the arm elements 306 to permit passage of the instrument "i". The arrangement of living hinges 306 may normally bias each respective arm element 306 radially inwardly relative to housing axis "m" such that the arm elements 306 capture and position the instrument "i" into aligned position with respect to the housing axis "m". FIG. 9 illustrates insertion of a relatively large diameter instrument "i" through centering mechanism 300 and the corresponding movement of arm elements 304, cam arms 310 and cam pins 312.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that the torsion spring 152 may be replaced, or supplemented, with internal leaf springs built into the arm elements to impart a radially inward force on the instrument. Other configurations are also envisioned.

What is claimed is:

1. A surgical access apparatus, which comprises:
    a housing member;
    a portal member extending from the housing member and defining a longitudinal axis, the housing member and the portal member defining a longitudinal passage therethrough dimensioned to permit passage of an elongated object;
    a centering mechanism mounted relative to the housing member, the centering mechanism including:
        an annular element mounted for rotational movement within the housing member and about the longitudinal axis;
        first and second arm elements mounted to the annular element and extending radially inwardly relative to the longitudinal axis, the first and second arm elements each positioned to intersect the longitudinal passage and adapted to pivot relative to the housing member, the first and second arm elements operatively connected whereby pivotal movement of the first arm element upon engagement with the elongated object causes the annular element to rotate in response thereto, and wherein the rotational movement of the annular element effects corresponding pivotal movement of the second arm element.

2. The surgical access apparatus according to claim 1 including a seal disposed within the housing member, the seal adapted to establish a substantial sealing relation with the elongated object.

3. The surgical access apparatus according to claim 1 wherein the first and second arm elements are normally biased to urge the instrument toward a generally aligned position with respect to the longitudinal axis.

4. The surgical access apparatus according to claim 1 wherein the centering mechanism includes a third arm element.

5. The surgical access apparatus according to claim 4 wherein the first, second and third arm elements are generally coaxially arranged with respect to the longitudinal axis.

6. A surgical access apparatus, which comprises:
    a housing member;
    a portal member extending from the housing member and defining a longitudinal axis, the housing member and the portal member defining a longitudinal passage therethrough dimensioned to permit passage of an elongated object;
    a centering mechanism mounted relative to the housing member, the centering mechanism including:
        an outer annular element, mounted for rotational movement within the housing member and about the longitudinal axis;
        first and second arm elements connected to the outer annular element and extending radially inwardly relative to the longitudinal axis, the first and second arm elements each positioned to intersect the longitudinal passage and adapted to pivot relative to the housing member, the first and second arm elements operatively connected whereby pivotal movement of the first arm element upon engagement with the elongated object causes the annular element to rotate in response thereto and effect corresponding pivotal movement of the second arm element.

7. The surgical access apparatus according to claim 6 wherein the first and second arm elements are adapted to pivot about respective pivotal axes upon rotation of the outer element.

8. A surgical access apparatus, which comprises:
    a housing member;
    a portal member extending from the housing member and defining a longitudinal axis, the housing member and the portal member defining a longitudinal passage therethrough dimensioned to permit passage of an elongated object;
    a centering mechanism mounted relative to the housing member, the centering mechanism including:
        an annular inner element mounted for rotational movement within the housing member and about the longitudinal axis;
        an outer mount,
        first and second arm elements pivotally mounted to the outer mount and extending radially inwardly relative to the longitudinal axis, the first and second arm elements each positioned to intersect the longitudinal passage and adapted to pivot relative to the housing member, the first and second arm elements operatively connected whereby pivotal movement of the first arm element upon engagement with the elongated object causes the annular inner element to rotate in response thereto and effect corresponding pivotal movement of the second arm element.

9. The surgical access apparatus according to claim 8 wherein the outer mount is fixed with respect to the housing member.

10. The surgical access apparatus according to claim 9 wherein the first and second arm elements are each pivotally mounted to the outer mount through a living hinge.

11. A surgical access apparatus, which comprises:
a housing member;
a portal member extending from the housing member and defining a longitudinal axis, the housing member and the portal member defining a longitudinal passage therethrough dimensioned to permit passage of an elongated object; and
at least three arm elements pivotally mounted relative to the housing member about respective pivot axes, each pivot axis extending in general parallel relation to the longitudinal axis, the at least three arms extending radially inwardly relative to the longitudinal axis, the at least three arm elements each positioned to intersect the longitudinal passage, the at least three arms having camming structure to operatively connect the at least three arms in a manner whereby pivotal movement of a first arm element upon engagement with the elongated object causes corresponding pivotal movement of the remaining arm elements.

12. The surgical access apparatus according to claim 11 including a seal disposed within the housing member, the seal adapted to establish a substantial sealing relation with the elongated object.

13. The surgical access apparatus according to claim 11 wherein the at least three arm elements are pivotally mounted relative to the housing member about living hinges.

14. The surgical access apparatus according to claim 11 wherein each of the at least three arm elements includes cam slots for receiving corresponding cam pins of adjacent arm elements.

15. The surgical access apparatus according to claim 11 wherein the at least three arm elements are adapted to normally bias the elongated object in a generally aligned position with respect to the longitudinal axis.

\* \* \* \* \*